United States Patent [19]

Moldowan

[11] Patent Number: 4,962,025
[45] Date of Patent: Oct. 9, 1990

[54] REAGENT ALCOHOL TEST STRIP DEVICE

[76] Inventor: Mervin J. Moldowan, 480 Benton View Dr., Philomath, Oreg. 97370

[21] Appl. No.: 28,022

[22] Filed: Mar. 17, 1987

Related U.S. Application Data

[63] Continuation of Ser. No. 815,809, Jan. 2, 1986, abandoned.

[51] Int. Cl.$^5$ .................. C12Q 1/26; G01N 31/22
[52] U.S. Cl. .......................... 435/25; 422/56; 422/57; 422/58; 435/805; 436/131; 436/132
[58] Field of Search .................. 422/55, 56, 57, 58; 436/131, 132, 170; 435/25, 805, 4

[56] References Cited

U.S. PATENT DOCUMENTS

| | | | |
|---|---|---|---|
| 2,167,304 | 7/1939 | Kloz | 422/56 X |
| 2,209,764 | 7/1940 | Cassen et al. | 436/131 X |
| 2,370,683 | 3/1945 | Palma | 422/61 |
| 2,785,958 | 3/1957 | Copenhefer et al. | 422/55 X |
| 2,865,718 | 12/1958 | Fowler | 422/57 X |
| 3,381,572 | 5/1968 | Tuwiner | 422/55 X |
| 3,644,177 | 2/1972 | Zyk | 435/805 X |
| 3,689,224 | 9/1972 | Agnew et al. | 435/810 X |
| 3,893,808 | 7/1975 | Campbell | 422/56 X |
| 4,108,729 | 8/1978 | Mennen | 422/56 X |
| 4,126,417 | 11/1978 | Edwards | 422/56 |
| 4,298,688 | 11/1981 | Kallies | 435/805 X |
| 4,486,536 | 12/1984 | Baker et al. | 422/58 X |
| 4,556,635 | 12/1985 | Hitzman et al. | 436/131 X |

Primary Examiner—Michael S. Marcus
Assistant Examiner—Jill Johnston

[57] ABSTRACT

A new method and apparatus for detection and analysis of substrates in a sample is described. The apparatus consists of a rigid or semi-rigid strip having a reaction site, a sample collector or metering site and color blocks to indicate the presence or amount of a substance in the sample. In another embodiment of the apparatus, useful for analysis of gases, a vessel is provided to wet the reaction site and prepare this site for analysis. The components of this device are all located on the same strip and bound together as a one piece test kit.

23 Claims, 1 Drawing Sheet

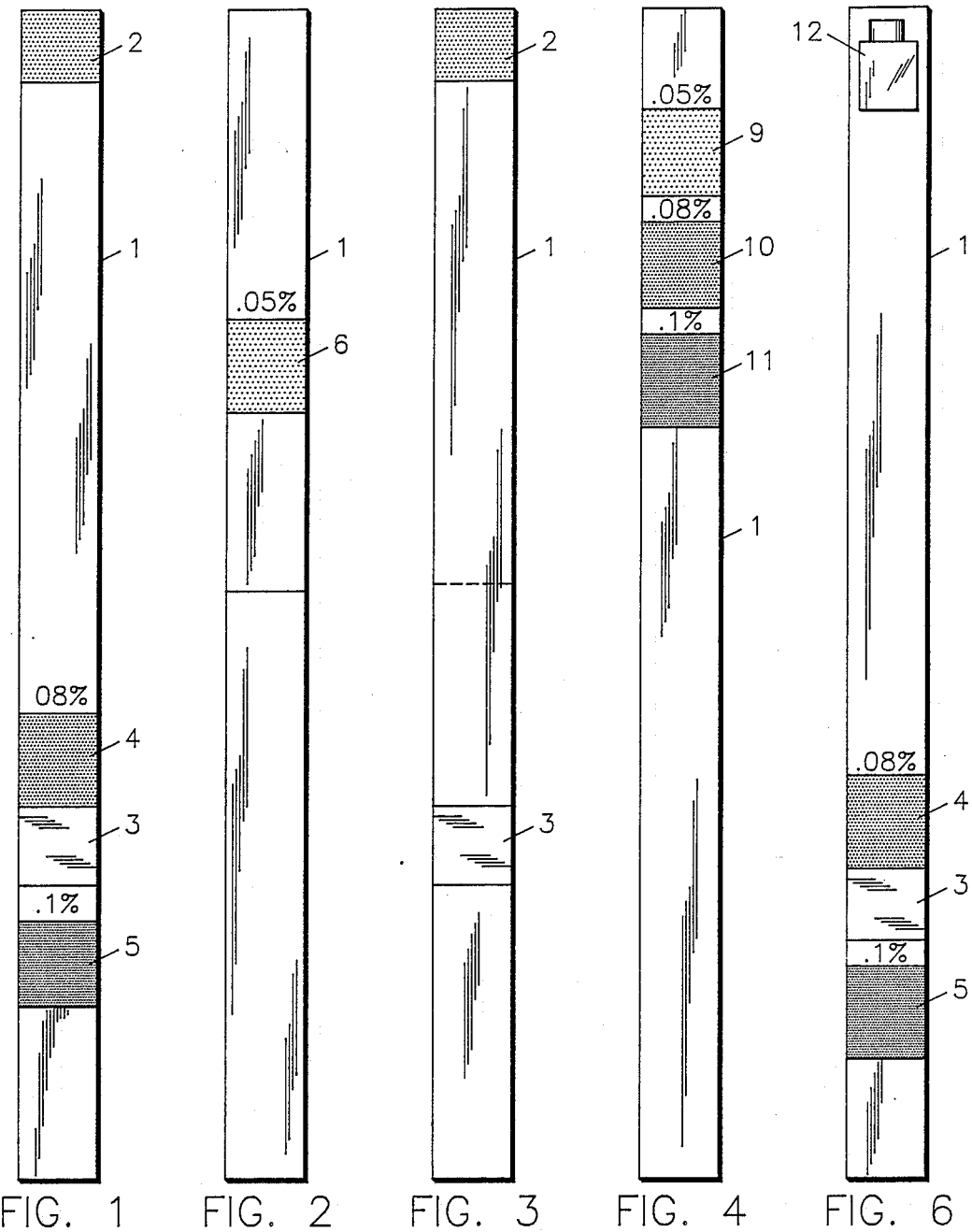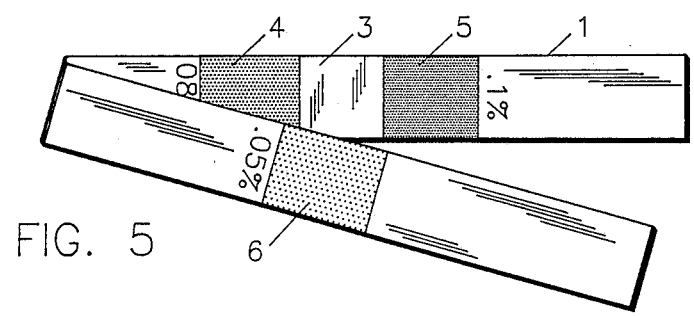

REAGENT ALCOHOL TEST STRIP DEVICE

This application is a continuation of Ser. No. 815,809, filed Jan. 1, 1986, now abandoned.

BACKGROUND OF THE INVENTION

The invention consists of an apparatus that aids in the analysis of substances. This device is a new and improved reagent test strip.

Various types of reagent test strips have been used to determine the chemical composition of biological samples or other types of materials. The analysis is done mostly by visual means, however instrumental methods can be employed to determine the quantity of chemical in the sample.

Reagent test strips are used to determine the content of various substances such as glucose, ketones, bilirubin, blood, urobilinogen, nitrite, ethanol or protein in biological samples. These strips are also used to detect or determine the quantity of chemicals such as chlorine, nitrite or ethanol in nonbiological samples.

These reagent test strips use chemicals and enzymes alone or in combination to determine the presence and relative concentration of a substance in a sample. The reagent test strip comprises a paper impregnated with the appropriate reagent chemicals or enzymes. This treated paper called the reaction pad is the tool used to detect or quantitate specific substances in a sample. The detection or analysis is started by exposing the reaction pad to the sample by placing the sample directly on the pad or by dipping the reaction pad into the sample. There are several variations of these reagent test strips in the prior art but they do not contain a feature to collect the sample and transfer it onto the reaction pad. The purpose of this disclosure is to describe a novel reagent test strip featuring a convenient method for collecting and transferring the sample onto the reaction pad.

Detecting the presence of a substance in a sample is based on a reaction pad color change, while the relative concentration of the substance in the sample is found by the intensity of the color change. The level of ethanol, glucose, ketones or other substances in the sample of unknown composition can be discerned from the color of the reaction pad when compared to a chart having colors representing specific levels of the appropriate chemical. Reagent test strips now in use contain color charts or color blocks that are seperate from the reagent test strip. These charts are normally printed on the package containing these strips. The separation of the color blocks from the reagent strips are inconvenient and a disadvantage. The present disclosure describes an improved reagent test strip that contains the color blocks on the reagent test strip itself for convenient comparison to the color change of the reaction pad. Analysis done by the reagent test strip kits now in use require at least four seperate components that are part of the kit and are necessary for substance analysis. These components comprise the reaction pad, attached to the strip, a color chart, a special blotter to absorb excess sample from the treated paper and a container to hold the sample. These components are not attached to the reagent test strip and must be assembled in a common area for chemical analysis. Once assembled the chemical or substance analysis can begin. This disclosure describes an apparatus that combines all these components into a one piece strip. Each component is attached onto the reagent test strip. This reagent test strip device eliminates assembly of a kit.

Analysis by reagent test strips now in use begins by dipping the test strip into the sample or bringing the sample in contact with the reaction pad in such a way that the reaction pad attached to the strip is exposed to the sample for analysis. With some types of samples, for example urine or saliva a container may be required to collect the sample so that the reagent test strip may be exposed to the sample. After removing the reagent test strip from the sample, it may be necessary in some cases to blot the reaction pad to remove excess sample. Following blotting, the relative concentration of the substance in the sample is found by comparing the color of the reaction pad to a color chart. The color chart found on test kits in the prior art are always seperate from the reagent test strip, while the new proposed reagent test strip device contains the color chart or color blocks on the reagent test strip itself.

SUMMARY OF THE INVENTION

The goal of this invention then is to eliminate seperate piecemeal components of a substance analysis kit and to provide a reagent test strip that contains all necessary test components on the strip itself. In addition this new device would contain a component to collect the sample and transfer the sample to the reaction pad for analysis. This new device would be used primarily for substance analysis of liquids but it should not be exclusively restricted to this use. The disclosure of this invention also describes a device that provides for substance analysis of gases such as air or breath.

BRIEF DESCRIPTION OF THE DRAWINGS

FIG. 1 is a front view of the inventive test strip.

FIG. 2 is a back view of the inventive test strip.

FIG. 3 illustrates the invention with an absorbent sample collector.

FIG. 4 is an illustration of the color chart.

FIG. 5 is an illustration of the test device color chart in use.

FIG. 6 is an alternative embodiment of the invention employing a vessel as the sample collector.

DETAILED DESCRIPTION OF THE INVENTION

FIG. 1 depicts the front view of my new device while FIG. 2 shows the back view of this new reagent test strip device. The device shown in FIG. 1 and FIG. 2 is a reagent test strip device constructed for ethanol analysis but similar devices could be constructed for other types of substance analysis. The supporting structure 1 is a rigid or a semi-rigid material to which the other components of the device 2, 3, 4, 5, and 6 are affixed. The preferred material used to make structure 1, and used in the ethanol reagent test strip device, is either paper or polystyrene. The claims to my patent are not to be construed so as to restrict it to these preferred materials. The dimensions of the structure by way of example only, for the ethanol reagent test strip device was ¼ inch wide and 4½ inches long, but the structure should not be restricted to these dimensions and the dimensions in any particular case would be dictated by the type of substance to be analyzed, or the method of sample collection.

Suitable material to collect a sample called a sample collector 2 is attached to the structure. In my preferred embodiment, the sample collector is located to one end of the rigid or semi-rigid strip. The dimension of the sample collector is proportional to the size of the reaction pad and to the volume of sample to be collected. For ethanol analysis, the size of the sample collector was 0.5 cm by 0.6 cm and a thickness of 0.5 cm. The choice of material that could be used to construct the sample collector would be dependant on a variety of factors, such as substance to be analyzed and presence of substances in the sample that may interfere with the operation of the device or reaction of substances of interest. For example, a polyurethane material could be used for analysis of extremely water soluble substances such as ethanol because ethanol would not absorb onto this material. Use of polyurethane as a sample collector has certain advantages since it absorbs oil soluble chemicals thereby not transfering interfering oil soluble compounds. However, polyurethane would not be selected to construct a sample collector for analysis of some oil soluble chemicals since these types of chemicals would be absorbed onto the sample collector. Therefore these types of chemicals would not be transferred to the reaction pad for analysis which would lead to incorrect results. The sample collector could contain additive(s) to counteract interfering substances before these substances could be transferred to the reaction pad. For example, the sample collector could contain enzymes such as esterases carbohydrases, proteases, oxidases, reductases, dehydrogenases or lipases to desroy interfering substances, sephadex or other absorbents to absorb unwanted chemicals or a weak buffer to destroy unwanted chemicals that are acid or base labile or reducing or oxidizing substances.

In summary the sampling component of this reagent test strip device called the sample collector could be used to perform several functions beside collecting and transfering the sample to the reaction pad for analysis.

Several methods could be used to transfer the sample from the sample collector to the reaction pad 3. The structure 1 could be constructed of flexible material so that the reagent test strip device could be bent to enable the sample collector to touch the reaction pad 3. This method would transfer the sample for analysis on the reaction pad. Another type of structure construction would be to perforate the structure marked 7. This perforation would make it easier to bend the structure or detach part of the structure containing the sample collector. For certain types of analysis a rigid structure may be required and perforation of the structure would allow bending of the rigid structure for sample transfer to the reaction pad. Another type of structure design and construction is to divide the structure marked 8 into two or more pieces. The structure could then be joined and hinged by flexible material for easy bending of the structure or detachment of the piece conatining the sample collector for transfer of the sample to the reaction pad.

The convenience of a sample collector on a reagent test strip can be demonstrated by the use of an ethanol reagent test strip device. Without a sample collector, the reagent test strip would be placed in the mouth to transfer saliva to the reaction pad, or the person would have to remove some saliva from the mouth to an intermediary position to place it on the reaction pad. With a sample collector such as with ethanol reagent test strip device, there is no need to remove saliva from the mouth onto an intermediary position or possibly place unwanted chemicals that are present in the reaction pad into the mouth. Similar advantages could be demonstrated for glucose reagent test strips, protein reagent test strips or many other types of reagent test strips that would contain a sample collector.

The sample collector also serves as a metering implement to transfer a measured volume of sample to the reaction pad. To construct a metering implement, the sample collector must be made to precise dimensions to transfer precise volumes of sample. The type of material, shape and size would dictate the quantity of sample that is absorbed and transfered to the reaction pad.

Reagent test strips can be used not only for simple detection but also for quantifying the relative concentration of a substance in samples. For example, a specific use for an ethanol or for a glucose testing strip device is to estimate levels of these substances found in saliva, urine, or blood. This can be done by first placing a small volume of a sample on the reaction pad. A color reaction occurs on the reaction pad. This color reaction is allowed to proceed for a limited time and the intensity of the color formed represents the relative quantity of the substance in the sample being tested. An estimate of ethanol or glucose in a sample is found by comparing the color of the reaction pad after a specific period of time to one or more color blocks such as blocks 4, 5 and 6. Each color block represents a certain substance level. Each color block contains a different color or shade and may be marked to indicate the level of the substance in the sample being analyzed. Each of these blocks represents a substance level and is attached to the reagent test strip. These color blocks could be any number of blocks and they could be located at any location on the structure so as to enable the user to conveniently make a color comparison. By way of example only, color blocks for ethanol analysis are shown in FIGS. 1, 2, 4, 5, and 6. Two color blocks are located at each end of the reaction pad, FIG. 1 marked 4 and 5. These blocks represent 0.08% and 0.1% blood ethanol levels respectively. An additional color block that represents 0.05% blood ethanol is located on the back of the reagent test strip on the back side of the structure FIG. 2 marked 6. This 0.05% color block is located in a position that when the structure is bent at the marking 7, the color block is adjacent to the reaction pad FIG. 1 marked 3 and shown in FIG. 5. When the structure is folded at 7 a color block appears below the reaction pad, a color block appears adjacent to the reaction pad and a color block appears above the reaction pad, FIG. 5. The placement of these color blocks around the reaction pad eases color comparison between the color blocks and the reaction pad. This is not the only arrangement of color blocks, since color blocks that represent various chemical levels may be placed on the structure in a multitude of ways. By way of example, all color blocks for a specific substance analysis can be placed on the back of the reagent test strip device FIG. 4 marked 9, 10 and 11. The structure could be perforated or divided then hinged for easy detachment of the piece containing the color blocks. The color block and structure once detached from the piece containing the reaction pad can be placed adjacent to the reaction pad for color comparison and substance level determination.

For manufacture of these reagent test strip devices, the color blocks could be printed in strips and then attached to the structure by various methods such as tape or glue. The color blocks in an alternate method could be printed directly on the structure in the preferred location. This method will eliminate the need for attachement of the color blocks to the structure.

In addition to substance analysis of liquid samples the reagent test strip devices can be used to detect substances in gases such as air or breath. Fluid as stated in the claims means a liquid, gas, air or breath sample. A common use for this device may be to detect the presence of ethanol in the breath of the user, such as may follow alcohol consumption. With one exception, analysis of gases with the reagent test strip device would be similar to the device for liquid analysis described above. It would not be necessary of course to provide a sample collector for analysis of gases. Instead, the sample collector would be replaced by a vessel to contain a liquid for wetting the reaction site to allow gas molecules to adhere to the reaction site. This vessel, FIG. 6 marked 12 may be attached to the structure of the reagent test strip device by a variety of methods such as adhesives. This vessel, 12, would be placed in the position once held by the sample collector. The purpose of the vessel for ethanol analysis is to contain a wetting solution and to transfer this solution to the reaction pad to make the chemical analysis possible on the reaction pad. For other types of analysis the wetting solution may also contain chemicals that participate in the reaction on the reaction site, or inhibit detection of undesired substances in the sample. All other parts of the proposed reagent test strip device for the analysis of gases would be similar to the proposed device for liquid and dipicted in FIGS. 1, 2, 3 and 4. One example of such a device is shown in FIG. 6. The size and shape of the vessel would be chosen according to the substance to be transferred to the reaction pad, and the size of the reaction pad. For detection or analysis of ethanol in breath, the vessel would contain 0.25 ml. of sterile distilled water. The volume of this vessel could vary from 0.001 mm$^3$ to 15 mm$^3$. The initial step to conduct analysis of gases would be to transfer the contents of the vessel to the reaction pad. This would be done in the same way a liquid sample would be transfered by the sample collector. When the vessel is near the reaction pad the contents of the vessel would be released by removing a stopper or crushing the vessel so that the contents spills onto the reaction pad.

Once this initial step is completed the reaction pad is ready for gas analysis. For detection or analysis of ethanol in breath the reaction pad is saturated with water before the device can detect the presence of ethanol in breath. When using the ethanol reagent test strip device, ethanol in the breath could be detected by blowing onto the wet reaction pad. The reaction pad for ethanol analysis contained alcohol oxidase and other chemicals.

I claim:

1. A test strip for the detection and determination of the concentration of alcohol in samples of fluids comprising:
   (a) a substrate to hold various pieces of a test strip in place,
   (b) a collection site attached to one end of the substrate consisting of a suitable material to absorb a sample to transfer to a reaction site,
   (c) a reaction site attached to the substrate in spaced relationship to the collection site, said reaction site containing alcohol metabolizing enzymes that will catalyze the oxidation of an alcohol and further containing additional, enzymes and reagents that will provide a visible response of a color change upon reaction with an alcohol, and
   (d) a color chart, respresenting specific alcohol concentrations, attached to the substrate to permit comparison of the color of the reaction site to determine the concentration of an alcohol in a fluid test sample.

2. The test strip of claim 1, where the color chart comprises two sites, one site on a reverse side of the substrate and another site adjacent the reaction site, and the substrate being bendable to permit the color chart to encompass the reaction site on three sides.

3. The test strip of claim 1, where the color chart is on a reverse side of the substrate and the substrate is perforated so the substrate would bend as to permit the color chart to be adjacent to the reaction site.

4. The test strip of claim 1, where the color chart is on a reverse side of the substrate and the substrate is divided then hinged so the substrate would bend as to permit the color chart to be adjacent to the reaction site;

5. The test strip of claim 1, where the collection site consists of material selected from the group consisting of polyurethane and cellulose.

6. The test strip of claim 1, where the substrate is sufficiently rigid to support the collection site, reaction site and color chart in place but flexible enough to permit the collection site to make contact with the reaction site.

7. The test strip of claim 1, where the substrate comprises material selected from the group consisting of paper and polystyrene;

8. The test strip of claim 1, where the alcohol metabolizing enzyme is alcohol oxidase.

9. The test strip for the detection and determination of the concentration of alcohol in samples of fluids comprising:
   (a) a substrate to hold various pieces of test strip in place,
   (b) a vessel attached to one end of the substrate positioned and constructed to contain wetting agents to be transferred to a reaction site to promote absorption of alcohol from a gaseous test sample,
   (c) a reaction site attached to the substrate in spaced relationship to the vessel and foldable into contact with the vessel, said reaction site containing alcohol metabolizing enzymes that will catalyze the oxidation of an alcohol and further containing additional enzymes and reagents that will provide a visible response of a color change upon reaction with an alcohol and,
   (d) a color chart, representing specific alcohol concentrations, attached to the substrate to permit comparision of the color of the reaction site to determine the concentration of an alcohol in a gaseous test sample.

10. The test strip of claim 9, where the color chart comprises two sites, one site on a reverse side of the substrate and another site adjacent the reaction site, and the substrate being bendable to permit the color chart to encompass the reaction site on three sides.

11. The test strip of claim 9, where the color chart is on a reverse side of the substrate and the substrate is perforated so the substrate will bend as to permit the color to be adjacent to the reaction site.

12. The test strip of claim 9, where the color chart is on a reverse side of the substrate and the substrate is divided then hinged so the substrate will bend as to permit the color to be adjacent to the reaction site.

13. The test strip of claim 9, where the substrate is sufficiently rigid to support the vessel, reaction and color chart in place but flexible enough to permit the collection site to make contact with the reaction site.

14. The test strip of claim 9, where the substrate comprises material selected from the group consisting of paper and polystyrene.

15. The test strip of claim 9, where the alcohol metabolizing enzyme is alcohol oxidase.

16. A test strip for the detection and determination of the concentration of alcohol in samples of fluids, comprising:
 (b) a collection site attached to one end of the substrate consisting of a suitable material to absorb a sample to transfer to a reaction site,
 (c) a vessel attached to the substrate in spaced relationship to the collection site and positioned and constructed to contain reagents for the detection of alcohol on a reaction site,
 (d) a reaction site attached to the substrate in spaced relationship to and foldable into contact with the collection site and the vessel, said reaction site containing alcohol metabolizing enzymes that will catalyze the oxidation of an alcohol and further containing additional enzymes and reagents that will provide a visible response of a color change upon reaction with an alcohol, and
 (e) a color chart, representing specific alchol concentrations, attached to the substrate to permit comparison of the color of the reaction site to determine the concentration of an alcohol in a fluid test sample.

17. The test strip of claim 16, where the color chart comprises two sites, one site on a reverse side to the substrate and another site of substrate and another site adjacent to the reaction site, and the substrate being bendable to permit the color chart to encompass the reaction site on three sides.

18. The test strip of claim 16, where the color chart is on a reverse side of the substrate the substrate is perforated so the substrate will bend as to permit the color chart to be adjacent to the reaction site.

19. The test strip of claim 16, where the color chart is on a reverse side of the substrate the substrate will bend as to permit the color chart to be adjacent to the substrate is divided then hinged so the substrate will bend as to permit the color chart to be adjacent to the reaction site.

20. The test strip of claim 16, where the collection site consists of material selected from the group consisting of polyurethane and cellulose.

21. The test strip of claim 16, where the substrate is sufficiently rigid to support the vessel, collection site, reaction site and color chart in place but flexible enough to permit the collection site to make contact with the combined reaction and detection site.

22. The test strip of claim 16, where the substrate comprises material selected from the group consisting of paper and polystyrene.

23. The test strip of claim 16, where the alcohol metabolizing enzyme is alcohol oxidase.

* * * * *